US00PP11087P

United States Patent [19]

Fear et al.

[11] Patent Number: Plant 11,087

[45] Date of Patent: Oct. 12, 1999

[54] RASPBERRY PLANT NAMED 'TOLA'

[75] Inventors: Carlos D. Fear, Aptos, Calif.; Mella-Dee M. Mayberry, Georgetown, Del.

[73] Assignee: Sweetbriar Development, Inc., Watsonville, Calif.

[21] Appl. No.: 09/019,174

[22] Filed: Feb. 5, 1998

[51] Int. Cl.[6] ..... A01H 5/00

[52] U.S. Cl. ..... Plt./204

[58] Field of Search ..... Plt./204

[56] References Cited

U.S. PATENT DOCUMENTS

P.P. 7,436 2/1991 Ackerman ..... Plt./204

*Primary Examiner*—Howard J. Locker
*Assistant Examiner*—Wendy A Baker
*Attorney, Agent, or Firm*—Pennie & Edmonds LLP

[57] ABSTRACT

The present invention relates to a new and distinct cultivar of red raspberry plant named 'Tola', botanically identified as *Rubus idaeus* L. The new cultivar is distinguished from other red fruited raspberry cultivars by its fruit of excellent flavor and color, its high yielding capacity (especially on the primocane crop), and its consistency in production of uniform size and shape of fruit. The new cultivar also has greater firmness than most other red fruited cultivars.

2 Drawing Sheets

BACKGROUND OF THE INVENTION

The new cultivar of raspberry plant was developed from the hybridization of the selection 'H374-2' (an unpatented variety) as the seed parent with the selection 'K589-1' (an unpatented variety) as the pollen parent. The parents were crossed in the Fall of 1991, whereafter fruit and seed were collected to produce seedlings for field planting in Watsonville Calif. in 1991. The new cultivar was selected from these seedlings in September 1992 for its excellent fruit firmness, fruit structure, and disease resistance. The new cultivar has been asexually propagated by in vitro shoot tip culture, root sucker divison and root cuttings at the Cassin Ranch in Santa Cruz County, Calif. and has been shown to maintain the desired and distinguishing characteristics after propagation over several generations.

SUMMARY OF THE INVENTION

The present invention provides a new and distinct cultivar of red raspberry plant named 'Tola'. The cultivar is botanically identified as *Rubus idaeus* L. The 'Tola' red raspberry plant produces a primocane crop which begins in mid to late July and continues until late October. The floricane crop begins in mid to late May and continues until mid July. Both the primocane and floricane yields are high relative to other comparable varieties. The fruit of 'Tola' is notably quite firm and very consistent with regard to its size and shape throughout its harvest period. The fruit of 'Tola' separates easily from its receptacle.

BRIEF DESCRIPTION OF THE DRAWINGS

The accompanying photographs show typical specimens of the primocane fruit, leaves and shoot of the new cultivar, in color as nearly true as it is reasonably possible to make in color illustrations of these characteristics.

DETAILED BOTANICAL DESCRIPTION

Figure 1:
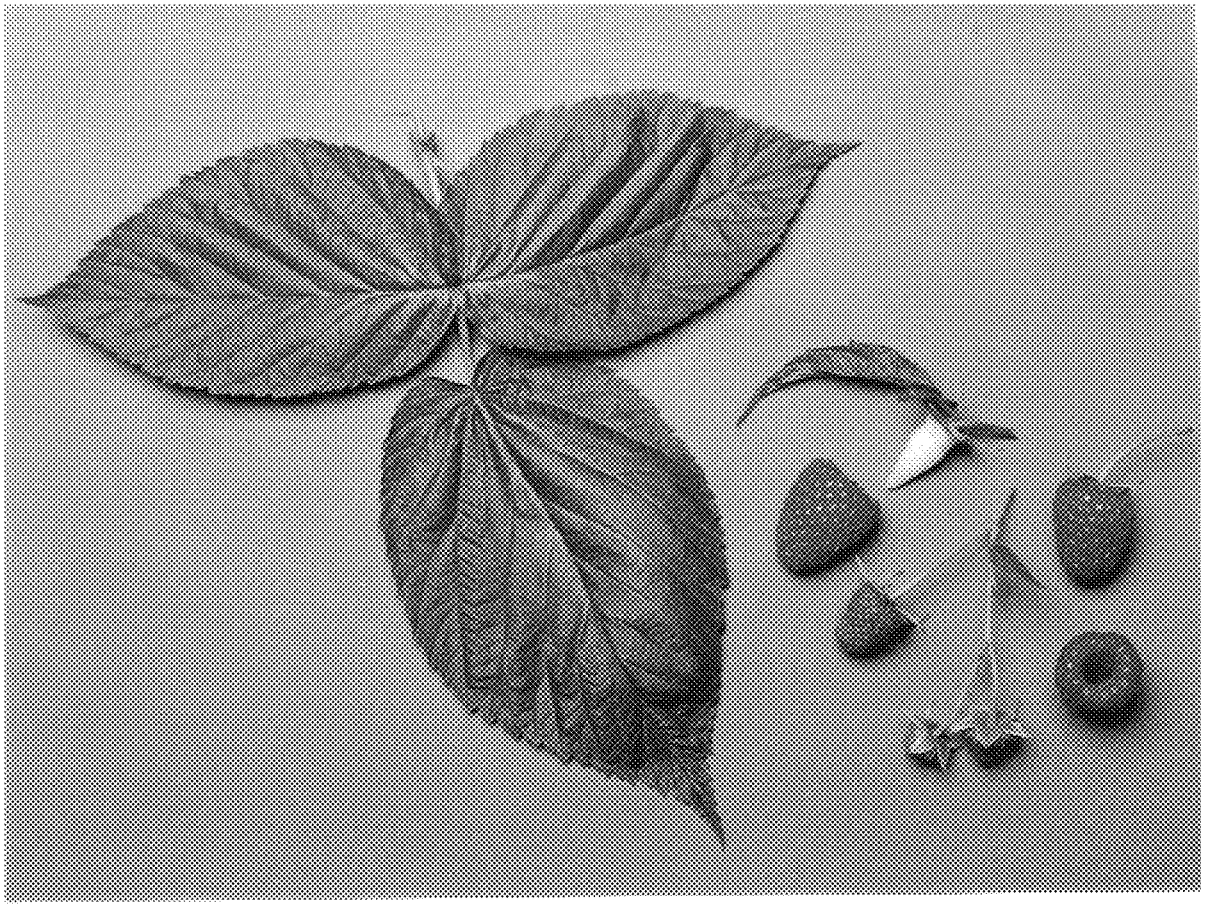
FIG. 1 is a photograph of a 'Tola' primocane mature leaf and fruit.
Figure 2:
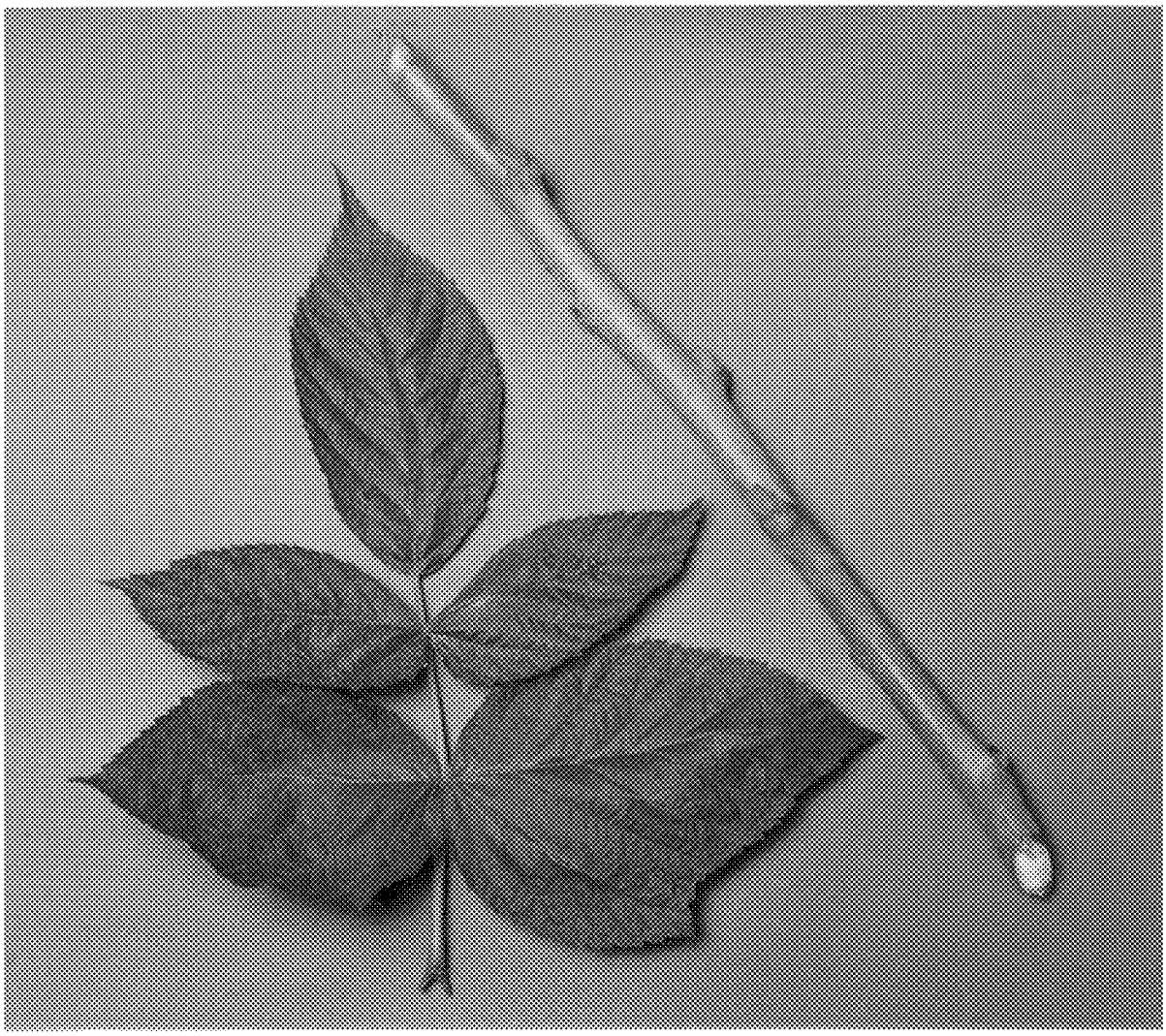
FIG. 2 is a photograph of a 'Tola' primocane shoot and leaf.

The following detailed description of the new raspberry cultivar, 'Tola', is based upon observations taken of plants and fruit grown in Watsonville, Calif. between 1994 and 1997, and is believed to apply to plants of the 'Tola' cultivar grown in similar conditions of soil and climate elsewhere.

Throughout this specification, color names beginning with a small letter signify that the name of the color, as used in common speech, is aptly descriptive. Color data beginning with a capital letter and followed by an alphanumeric code designating the color according the The R.H.S. Colour Chart published by The Royal Horticultural Society of London, England. Color designations, color descriptions, and other phenotypical descriptions may deviate from the stated values and descriptions depending upon variation in environmental, seasonal, climatic and cultural conditions.

Tables 1and 2 provide information on the plant and fruit characteristics of the new cultivar 'Tola' compared with with characteristics of the unpatented raspberry cultivars 'Heritage', 'Summit' and 'Amity'. The cultivars closest to the new 'Tola' cultivar are 'Amity' for fruit size and 'Summit' for its fruiting cycles. Observations of the cultivars were taken under similar conditions.

The new variety is particularly characterized and distinguished from other cultivars by its fruit firmness, fruit structure, yield, and disease resistance.

The fruit color of 'Tola' is a medium red at harvest but darkens after harvest to a deeper color. Fruit of 'Tola' separates easily from the receptacle and is of excellent firmness at harvest. The fruit of 'Tola' is very consistent in size and shape throughout the harvest period.

The primocane and floricane yields of 'Tola' are high relative to the varieties 'Amity' and 'Heritage'.

'Tola' is distinguishable from its pollen parent, selection 'H374-2', by producing a higher yield of fruit and having shinier, brighter fruit. The new cultivar is distinguished from its seed parent, selection 'K589-1', by having smaller and firmer fruit.

ISOZYME ANALYSIS

In addition to the morphological description above, the new cultivar 'Tola' has been analyzed to obtain an indication of its genetic makeup to provide further means for identifying the new variety and distinguishing it from some other somewhat similar and/or related raspberry varieties. Specifically, leaf samples of 'Tola', and the unpatented varieties 'Summit' and 'Heritage' were analyzed by electrophoresis for isozyme patterns of the enzymes phosphoglucoisomerase (PGI), malate dehydrogenase (MDH) and phoshpoglucomutase (PGM) according to the procedure described by J.C. Cousineau and D.J. Donnelly, "Use of isozyme analysis to characterize raspberry cultivars and detect cultivar mislabeling", *Hort Science*27:1023–1025 (1992). Isozyme characterization of the cultivar 'Tola' is presented in Table 3, with the letters representing the banding patterns for each enzyme as designated in the above-identified article.

DISEASE AND STRESS RESISTANCE

The cultivar has very high resistance to late leaf rust. Resistance is unknown to powdery mildew and root rots. Cold tolerance of the new cultivar has not been established. Post harvest fruit rot resistance is good in comparison over many selections and varieties.

TABLE 1

PLANT CHARACTERISTICS OF 'TOLA'

| | Tola | Heritage | Summit | Amity |
|---|---|---|---|---|
| General | | | | |
| Plant size | large | large | small-medium | medium |
| Growth habit | erect | erect | semi-erect | erect |
| Productivity | very high | medium | high | low-medium |
| Self-fruitfulness | self-fruitful | self-fruitful | self-fruitful | self-fruitful |
| Primocane fruiting | | | | |
| percent of cane length flowering as primocane | ~40–50 | ~5–20 | ~40–50 | ~20–35 |
| percent of total yield | ~50–60 | ~40–60 | ~50–70 | ~40–50 |
| Number of young shoots | many | medium | few | many |
| Primocanes | | | | |
| number fruiting laterals/cane | 9–22 (mean 16) | 2–14 (mean 8) | 9–15 (mean 12) | 6–14 (mean 10) |
| number of canes/crown | 1–5 (mean 3) | 3–5 (mean 4) | 2–7 (mean 3) | 1–6 (mean 3) |
| young shoot pigmentation | medium intensity red | medium intensity red | medium intensity red | medium intensity red |
| length (cm) | 162–243 (mean 193) | 182–230 (mean 208) | 137–212 (mean 164) | 135–208 (mean 168) |
| diameter (end of 1st year) | | | | |
| cane base (cm) | 1.0–1.8 (mean 1.4) | 0.9–1.4 (mean 1.2) | 0.8–1.3 (mean 1.1) | 0.8–1.5 (mean 1.1) |
| central ⅓ of cane (cm) | 0.7–1.3 (mean 1.1) | 0.8–1.1 (mean 1.0) | 0.7–1.0 (mean 0.8) | 0.6–1.0 (mean 0.8) |
| time of shoot emergence | medium | very late | late | medium |
| prickles | | | | |
| pigmentation | green-brownish green | green-brownish green | brownish purple-purple | purple |

TABLE 1-continued

PLANT CHARACTERISTICS OF 'TOLA'

| | Tola | Heritage | Summit | Amity |
|---|---|---|---|---|
| density on young shoots | medium | dense | sparse | sparse |
| attitude of tip | downward | downward | downward | horizontal |
| size | small | medium | medium | small |
| texture | soft | rigid | heavy | heavy |
| presence and distribution on petioles | regularly distributed | regularly distributed | regularly distributed | regularly distributed |
| pubescence on canes | strong | absent or very weak | medium | medium |
| internodal distance (cm) | | | | |
| (at central ⅓ of cane) | 3.5–6.5 (mean 5.2) | 3.0–6.0 (mean 4.7) | 3.2–7.5 (mean 4.8) | 3.0–6.5 (mean 5.0) |
| lenticels | not visible | not visible | not visible | not visible |
| Floricanes | | | | |
| number nodes/lateral branch | 12–20 | 10–14 | 10–15 | 12–19 |
| number of flowers/node | 2–4 | 1–4 | 2–6 | 1–2 |
| Leaves | | | | |
| Arrangement | compound | compound | compound | compound |
| Relief between veins | weak | very weak | medium | medium |
| Cross section | concave | concave | flat | concave-flat |
| Leaflet number | usually 5 | 3–5 | usually 5 | usually 3 |
| Terminal leaflet | | | | |
| length (cm) | 11.6 | 14.6 | 12.4 | 13.7 |
| width (cm) | 7.5 | 7.8 | 7.2 | 12.1 |
| shape | ovate | ovate | ovate | lobed |
| tip | acuminate | acuminate | acuminate | acuminate |
| base | cordate-round | acute | rounded | cordate |
| margin | doubly serrate | doubly serrate | doubly serrate | doubly serrate |
| Lateral leaflets (basal pair) | | | | |
| overlap | touching | free | overlapping | overlapping |
| orientation | opposite | opposite | opposite | opposite |
| shape | oblique | oblique | ovate-lobed | ovate-lobed |
| tip | acuminate | acuminate | acuminate | acuminate |
| base | oblique | oblique | oblique-rounded | oblique |
| margin | doubly serrate | doubly serrate | doubly serrate | doubly serrate |
| length (cm) | 11.9 | 14.7 | 11.6 | 11.7 |
| width (cm) | 7.6 | 8.6 | 7.7 | 8.2 |
| Rachis length | 1.0–1.8 | 0.8–2.2 | 0.5–1.8 | 2.4–3.9 |

TABLE 1-continued

PLANT CHARACTERISTICS OF 'TOLA'

| | Tola | Heritage | Summit | Amity |
|---|---|---|---|---|
| between terminal leaflet and adjacent lateral leaflets (cm) | (mean 1.4) | (mean 1.5) | (mean 1.2) | (mean 3.0) |
| Glossiness | medium | medium | medium | dull |
| Color | | | | |
| face | medium 137A | medium 137A, 139A | medium 137A | medium 147A |
| underside | 138B | 148C, 191B | 191B | 191A |
| Petiole | | | | |
| length (cm) | 4.0–10.0 (mean 7.1) | 6.6–8.5 (mean 7.6) | 5.8–8.9 (mean 7.4) | 4.0–8.2 (mean 6.0) |
| pigmentation of upper surface | unpigmented | lightly | lightly | lightly |
| pigmentation of underside | unpigmented | unpigmented | lightly | unpigmented |
| Petiolule length | short | very short | short | very short |
| Stipule orientation | erect | erect | erect-clasping | erect-clasping |
| Flowers | | | | |
| Flower color | white | white | white | white |
| Flowering period | | | | |
| primocane | mid June-late September | mid June-early October | early June-mid September | early June-early October |
| floricane | early April-early June | early April-early June | early April-early June | early to mid March-early June |
| Flower size | small | small | medium | large |
| Petal | | | | |
| length (cm) | 0.6–0.8 | 0.7–0.8 | 0.7–0.9 | 0.7–1.0 |
| width (cm) | 0.3–0.4 | 0.3 | 0.3–0.4 | 0.3–0.5 |
| Pedicel | | | | |
| coloration | absent or very weak intensity, red | present, strong intensity, red | present, strong intensity, red | present, strong intensity, red |
| length | short | medium | medium | long |
| Productivity | | | | |
| Primocane | ~9.2 t/acre | ~5.1 t/acre | ~7.3 t/acre | ~6.4 t/acre |
| Floricane | ~4.1 t/acre | ~4.1 t/acre | ~2.9 t/acre | ~5.1 t/acre |

TABLE 2

FRUIT CHARACTERISTICS OF 'TOLA'

| | Tola | Heritage | Summit | Amity |
|---|---|---|---|---|
| Fruit | | | | |
| Harvest season | | | | |
| primocane | mid to late | late July- | mid July- | mid July- |

TABLE 2-continued

FRUIT CHARACTERISTICS OF 'TOLA'

| | Tola | Heritage | Summit | Amity |
|---|---|---|---|---|
| | July-late October | mid November | late October | mid November |
| floricane | mid to late May - mid July | mid May-mid July | mid May-mid July | late April -mid July |
| Color | Medium Red | Medium Red | Medium Red | Medium Red |
| immature | 44B | 53A | 46A | 46A |
| maturing | 45A–47A | 45A, 46D | 45A | 47A |
| mature | 46A, 46B | 44C | 42B | 42B |
| Glossiness | medium | medium | medium | medium |
| Dimensions | | | | |
| weight (g/fruit) | | | | |
| primocane | 2.9–3.6 (mean 3.3) | 2.7–2.9 (mean 2.8) | 2.5–3.3 (mean 2.8) | 2.7–3.7 (mean 3.2) |
| floricane | 2.8–3.5 (mean 3.1) | 2.3–2.7 (mean 2.6) | 2.5–2.8 (mean 2.6) | 3.0–3.4 (mean 3.2) |
| length (primocane) (mm) | 15.9–25.4 (mean 22.4) | — | 17.5–25.4 (mean 20.2) | 17.5–22.2 (mean 20.1) |
| width (primocane) (mm) | 17.5–23.8 (mean 20.9) | — | 18.3–23.0 (mean 20.4) | 15.9–23.0 (mean 20.2) |
| Soluble solids (%) | 9.2 | — | 9.4 | 9.7 |
| Titratable acidity | | | | |
| (% as citric acid) | 11.8 | — | 14.5 | 11.2 |
| Seeds | | | | |
| weight (mg) | 1.5 | — | 1.8 | 1.5 |
| Number | 93–154 | 45–102 | 73–119 | 62–108 |
| druplets/fruit | (mean 127) | (mean 72) | (mean 98) | (mean 88) |
| Firmness | firm | firm | firm | firm |
| Yield | high | medium | high | medium |

TABLE 3

ISOZYME BANDING PATTERNS OF 'TOLA' COMPARED WITH 'HERITAGE' AND 'SUMMIT'

| | Isozyme and Pattern | | |
|---|---|---|---|
| Cultivar | PGI | MDH | PGM |
| Tola | A | C | C |
| Heritage | A | D | C |
| Summit | A | C | A |

We claim:

1. A new and distinctive cultivar of raspberry plant as illustrated and described herein.

* * * * *